US006547833B2

(12) United States Patent
Casperson et al.

(10) Patent No.: US 6,547,833 B2
(45) Date of Patent: *Apr. 15, 2003

(54) TWO-PART AQUEOUS COMPOSITION FOR OXIDATIVE COLORATION OF HAIR

(75) Inventors: Stephen Casperson, Milford, CT (US); Zubaida Khan, Stamford, CT (US); Slavica Grogin, Trumbull, CT (US); Kue-Yick Lee, Stamford, CT (US)

(73) Assignee: Clairol Incorporated, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/791,535

(22) Filed: Feb. 23, 2001

(65) Prior Publication Data

US 2002/0157191 A1 Oct. 31, 2002

(51) Int. Cl.$^7$ .................................................. H61K 7/13
(52) U.S. Cl. ...................... 8/405; 8/406; 8/407; 8/409; 8/410; 8/411
(58) Field of Search ........................... 8/405, 406, 407, 8/409, 410, 411

(56) References Cited

U.S. PATENT DOCUMENTS

| | | | |
|---|---|---|---|
| 3,303,213 A | 2/1967 | Kalopissis et al. | 260/534 |
| 3,331,781 A | 7/1967 | Kalopissis et al. | 252/152 |
| 3,436,167 A | 4/1969 | Kalopissis et al. | 8/10.1 |
| 3,891,385 A | 6/1975 | Kalopissis et al. | 8/10.1 |
| 3,986,825 A | 10/1976 | Sokol | 8/10.1 |
| 4,240,450 A | 12/1980 | Grollier et al. | 132/7 |
| 4,362,528 A | 12/1982 | Grollier et al. | 8/406 |
| 4,402,700 A | 9/1983 | Feinland et al. | 8/416 |
| 4,532,127 A | 7/1985 | Feinland | 424/62 |
| 4,563,188 A | 1/1986 | Bugaut et al. | 8/410 |
| 4,663,157 A | 5/1987 | Brock | 424/59 |
| RE33,786 E | 1/1992 | Pohl et al. | 4/406 |
| 5,137,538 A | 8/1992 | Madrange et al. | 8/410 |
| 5,376,146 A | 12/1994 | Casperson et al. | 8/408 |
| 5,393,305 A | 2/1995 | Cohen et al. | 8/406 |
| 5,968,493 A | 10/1999 | Dornoff | 424/70.1 |
| 5,976,195 A | 11/1999 | De la Mettrie et al. | 8/411 |
| 6,022,381 A | 2/2000 | Dias et al. | 8/406 |
| 6,074,439 A | 6/2000 | De la Mettrie et al. | 8/411 |
| 2001/0002254 A1 | 5/2001 | Duffer et al. | 424/70.1 |

FOREIGN PATENT DOCUMENTS

| | | | |
|---|---|---|---|
| EP | 0 938 888 A2 | 9/1999 | A61K/7/00 |
| EP | 0 952 817 B1 | 7/2001 | A61K/7/48 |
| JP | 11217319 | 8/1999 | A61K/7/13 |
| WO | 02/00177 A2 | 1/2002 | A61K/7/00 |

OTHER PUBLICATIONS

*Household and Personal Products Industry*, April 2000, p. 20.
International Cosmetic Ingredient Dictionary and Handbook, Eighth Edition (CTFA 2000), pp. 25–28.
Jachowicz et al.; "Acrylates/Beheneth–25 Methacrylate Copolymer (Aculyn® 28)"; *Cosmetics & Toiletries Manufacture Worldwide*; vol. 10, pp. 258–269 (2000).
*Household and Personal Products Industry*, vol. 37, No. 6, p. 18 (2000).
"Aculyn® 28: A Cost–Effective & Versatile Rheology Modifier"; *Application Alert*, Nov. 2000.

Primary Examiner—Yogendra N. Gupta
Assistant Examiner—Eisa Elhilo
(74) Attorney, Agent, or Firm—Charles J. Zeller

(57) ABSTRACT

A two-part high aqueous-content system for oxidative coloration of hair utilizing a developer formulation of water, a peroxide oxidizer and an anionic acrylate/beheneth-25 methacrylate copolymer. The system has efficient conditioning properties and substantially less or no dry-out problems.

24 Claims, No Drawings

TWO-PART AQUEOUS COMPOSITION FOR OXIDATIVE COLORATION OF HAIR

FIELD OF THE INVENTION

This invention relates to high aqueous-content hair coloring compositions with good thickening and conditioning properties with minimized drying effects.

BACKGROUND TO THE INVENTION

When oxidation dyes of the type comprising primary intermediates and couplers are used in the dyeing of human hair, the procedure usually involves the use of a two part system. One part is the lotion formulation which contains a variety of ingredients, including the oxidation dye precursors, and forms a gel immediately prior to application to the human hair, when mixed with the second part which is the developer formulation containing a suitable oxidizing agent. The developer usually contains an oxidizing agent, such as hydrogen peroxide and as a consequence some of the natural melanin pigment of the hair may be initially destroyed. The precursors in the lotion penetrate into the hair and are oxidized to produce the desired color. Such systems will generally contain 50% or more of organic solvents and surfactants, and require relatively high levels of dye precursors to produce the desired color.

Several conditions are important for the procedures using oxidative dyes to work properly. These include the following.

1. The formulations must be stable to insure a reasonable shelf life.
2. The compositions formed by mixing the lotion and developer must have rheological properties whereby application, either by use of a brush or with the fingers, can readily distribute the dye throughout the hair mass and yet in the absence of stress, dripping or running from the hair during the color development period can be substantially avoided.
3. The dye mixture, as applied to the hair, should allow rapid diffusion of the dye precursors from the dye mixture into the hair fiber.
4. The mixture, while thick enough to stay in place during the color development period, should be readily rinseable from the hair with water.
5. The mixture should preferably contain conditioning agents that leave the hair in a condition such that it is easy to detangle while wet and also feel smooth and be readily managed when dry.
6. The lotion and developer should preferably, but not necessarily, have comparable viscosities in order to facilitate mixing.
7. The dyeing effect should be rapid, with a dyeing time preferably under thirty minutes In conventional permanent hair dye products, the rheological properties have generally been attained by the use of a dye lotion containing a high level of surfactants and organic solvents to provide a thin lotion which, on mixture with a highly aqueous developer solution of the oxidizing agent, forms a dye mixture with the desired gel-like consistency. The disadvantage of this approach is that the dye mixture still contains a high level of surfactants that tend to retard the diffusion of the dye precursors into the hair. The preferred surfactants in commercial products have been nonionic or anionic materials that do not provide any conditioning. The preferred conditioners for human hair are cationic surfactants that provide excellent conditioning but are incompatible with anionic surfactants.

There have been many efforts to produce oxidative hair dyeing compositions having the desired properties, listed above, while at the same time avoiding the aforesaid problems.

U.S. Pat. Nos. 3,303,213; 3,331,781; 3,436,167 and 3,891,385 describe the use, in hair treating compositions, of specific amphoteric surfactants such as the sodium salt of $N$-($N^1,N^1$-dimethyl-aminopropyl)-$N^2$-alkyl (fatty) aspartagine wherein the "fatty" moiety is derived from the fatty acids of tallow. According to the patents, the amphoteric surfactant can be employed with organic solvents and any of a variety of cationic, anionic or non-ionic surface active agents. There is no indication of the use of quaternary ammonium salts in the compositions.

U.S. Pat. No. 4,402,700 describes hair dyeing compositions containing quaternary ammonium compounds and also cites the possible uses of amphoteric surfactants in the compositions. These compositions, however, require the uses of organic solvents and nonionic surfactants, and the amount of water in the compositions is less than 50%.

U.S. Pat. No. 4,532,127 describes hair coloring compositions containing oxidative dyes together with an oxidizing agent. The compositions require the presence of quaternary amine compounds containing two long chain alkyl radicals each having about 10 to 26 carbon atoms. Any of a variety of surfactants may be present in the composition that, although they have a high water content may contain organic solvents. The lotions of the patent contain di-long chain alkyl quaternary ammonium compounds in the presence of relatively large amounts of non-ionic surfactants. They are said to be superior to a comparison lotion containing a mono-long chain alkyl quaternary ammonium compound in combination with an amphoteric surfactant. The lotions of this patent suffer from the disadvantage of having high levels of surfactant thus inhibiting rapid diffusion of the dye precursors into the hair. Furthermore, di-long chain alkyl quaternary ammonium compounds are poorly biodegradable, particularly as compared to the mono-long chain alkyl quaternary ammonium compounds. The compositions disclosed are free of anionic surfactants and anionic polymers.

U.S. Pat. No. 4,663,158 describes hair conditioning compositions containing an amphoteric surfactant together with at least one quaternary cationic polymer such as poly (methacrylamidopropyl)trimethy ammonium chloride. The compositions are acidic.

U.S. Pat. No. 4,563,188 discloses hair dyeing compositions containing specific para-phenylenediamine derivatives which may contain any of several types of surfactants as well as organic solvents.

U.S. Pat. No. 5,137,538 describes oxidative hair dyeing compositions containing specific para phenylenediamines and $N,N^1$-diphenylalkylenediamines. The compositions may be acidic or alkaline. They may contain organic solvents and anionic, cationic, non-ionic or amphoteric surfactants.

U.S. Pat. No. 4,362,528 refers to compositions said to be useful for hair coloring. These compositions comprise oxidative dyes together with any of a variety of cationic polymers. The hair is first treated with such composition and subsequently rinsed with a shampoo composition containing an anionic detergent.

U.S. Pat. No. 4,240,450 describes hair treating mixtures such as shampoos and hair coloring compositions which may be oxidative. The compositions include cationic and anionic polymers that may be chosen from hundreds of such polymers which are generically and specifically described.

U.S. Pat. No. 3,986,825 refers to a variety of hair coloring composition which may be employed with either oxidizing agents or reducing agents and which employ any of a wide variety of surfactant water soluble polymer additives together with anionic, cationic, nonionic or amphoteric surfactants.

U.S. Pat. No. RE. 33786 teaches that rapid dyeing with highly aqueous compositions can be achieved through the use of a certain acrylate copolymer viz an acrylate/steareth-20 methacrylate copolymer in the developer. A similar system employing a certain anionic copolymer of acrylic acid or methacrylic acid with their lower alkyl esters is disclosed in U.S. Pat. No. 5,393,305. Also, in U.S. Pat. No. 5,376,146 the use of a combination of anionic acrylic polymers, such as the copolymers of both RE No. 33786 and U.S. Pat. No. 5,393,305, is disclosed. In U.S. Pat. Nos. 5,976,195 and 6,074,439 the use of anionic polymers containing at least one allyl ether unit is taught to improve gelling properties of such hair coloring compositions. Such polymers produce a thickening effect only when the developer is added to the alkaline lotion containing the color precursor. The disadvantage of the use of acrylate copolymers, or any other anionic polymer, as used in these patents is that they tend to deactivate quaternary ammonium conditioning compounds by complexation. Furthermore, products containing a simple aqueous acrylate system are difficult to rinse from the hair. Additionally, experience has shown that lotions and developers containing the specific anionic polymers of U.S. Pat. No. Re. 33786, U.S. Pat. Nos. 5,393,305, 5,376,146, 5,976,195 and 6,074,439 are generally difficult to formulate in that the viscosity of the resulting mixture is generally not readily controllable. Moreover, the rheology profile is such that high levels of polymer solids and the use of combinations of polymers is required to achieve cosmetically acceptable products. Another feature of the use of these suggested polymeric products is that they have a tendency to "dry", creating an undesirable surface residue or film. Additionally, such products containing these polymers generally do not possess sufficient long-term storage stability properties. A further drawback is that use of these suggested polymers is that a generally high level of polymer is required.

It is an object of this invention to provide stable hair dyeing compositions which avoid the aforesaid problems while at the same time providing high aqueous content, acceptable rheological profile, rapid dyeing permanent hair coloring systems having a minimized drying effect and improved storage properties, and exhibiting excellent conditioning properties. A further object of this invention is to produce such composition employing low levels of active/solids of the anionic polymer in the developer solution which when combined with the dye base solution produces an ideal viscosity.

It is a further object of the invention to provide lotion and developer formulations which can be readily formed into a gelled mixture having an appropriate viscosity to remain on the hair for a sufficient period to achieve the desired hair coloring effect.

It is yet another object of this invention to provide hair coloring compositions that provide excellent sheer-down during mixing of the lotion and developer portions to permit easily intermingling of the developer solution with the lotion containing the dye base components, i.e., the primary intermediates and couplers.

It is a still further object of this invention to a provide hair coloring composition which also impart a durable, more efficient conditioning effect to treated hair and which markedly improves its compatibility without the need of an anionic shampoo as a post-dyeing step.

BRIEF SUMMARY OF THE INVENTION

The invention comprises a developer formulation of an oxidizer, an anionic acrylate/beheneth-25 methacrylate coplymer and at least about 70% by weight water. The invention also comprises a two-part hair dyeing composition comprising such a developer formulation and a lotion formulation comprising oxidizable dye precursors and at least about 70% by weight water.

This invention comprises a two-part system comprising aqueous, oxidative, hair coloring compositions (lotions and developers) for mixture with each other shortly before use to form a gel. The lotion comprises an aqueous alkaline composition having a pH of from about 7 to 11 and a water content of at least about 70% by weight, a tinctorily effective amount of oxidative dye precursors, at least one anionic or amphoteric surfactant or mixture thereof and at least one cationic polymer. The second part, i.e. the developer is an aqueous composition with a pH of from about 2 to about 6, preferably 2 to 3. It contains a peroxide oxidizing agent and at least one substantially water insoluble anionic polymer which is solubilized on admixture of the lotion and developer and where the anionic polymer is an acrylate/beheneth-25 methacrylate copolymer.

The invention also comprises a kit or package of the developer and lotion formulations. A further aspect of this invention is the use of such two-part system for the oxidative coloration of hair.

DETAILED DESCRIPTION OF THE INVENTION

The components in the aqueous first part of the compositions of this invention, i.e. the lotion, include water, the oxidizable dye precursors, an anionic, nonionic or amphoteric surfactant or mixture thereof and a cationic polymer. The water content of the composition is at least about 70% by weight and may be as high as 95% or higher.

Unless otherwise specified the amounts of the various ingredients in the compositions of this invention are in percent by weight based on the total weight.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1–3.

Suitable nonionic surfactants are any suitable nonionic surfactants that have an HLB of from about 3 to about 14. The abbreviation "HLB" stands for hydrophilic lipophilic balance and is described in detail in "The HLB System, A Time Saving Guide to Emulsifier Selection", ICI Americas Inc., August 1984. Examples of suitable nonionic surfactants include, but are not limited to, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol Amphoteric surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group. There are a large number of amphoteric surfactants that are suitable for use in this invention. They include, for example, the asparagine derivatives identified in the first three patents mentioned above as well as a variety of well-known betaines, sultaines, glycinates and propionates which may be represented by the following structural formulas:

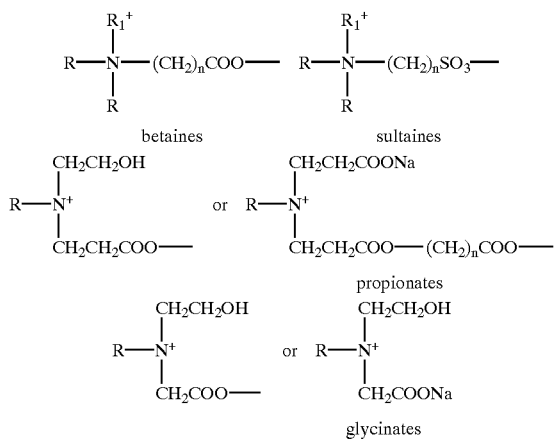

betaines   sultaines propionates glycinates

In the formulas, R is an alkyl or alkylamido group containing from about 10 to about 20 carbon atoms, R, $R_1$, $R_2$ and $R_3$ are alkyl or hydroxyalkyl groups, which may be the same or different, and contain up to about five carbon atoms and n is a positive integer up to about five.

Typical amphoteric surfactants that are suitable for use in this invention include: lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The anionic and amphoteric surfactants and mixtures of these surfactants for use in this invention may be selected from any of a number of known surfactants. The amount of such surfactants in the compositions is normally from about 0.5% to 15% by weight, preferably 2% to 8% by weight.

The amphoteric surfactants presently preferred for use in this invention are: cocamidopropyl betaine, coco-betaine, stearyl betaine, cocoamphocarboxyglycinate, cocoamphodipropionate, and stearoamphoglycinate.

The pH of the lotions of this invention will generally be from about 7 to about 11. It is preferred, however, that this pH be in the range of 7.5 to 9.5.

Any of a wide variety of alkaline agents can be used to adjust the pH of the hair coloring compositions. Ammonium hydroxide, because of its freedom from toxicity over a wide concentration range and its economy, is an acceptable alkalizing agent. However, there can be used in place of, or together with, ammonium hydroxide any other compatible ammonia derivative as an alkalizing agent, such as an alkylamine, for example ethylamine, or triethylamine; or alkanolamines, for example ethanolamine, diethanolamine, aminomethyl propanol, aminomethyl propanediol and trishydroxymethyl aminomethane. Likewise, any other of the organic or inorganic alkalizing agents may be used, such as sodium or potassium hydroxide, sodium or potassium carbonate, sodium phosphate, sodium hydrogen phosphate, sodium silicate, guanidine hydroxide and the like. The preferred alkaline reagents are ammonium hydroxide, sodium carbonate and ethanolamine.

With the agents listed above, the selected pH will generally be achieved if the lotion contains from about 0.1% to 5% by weight of alkaline agent.

The oxidative dye precursors employed in the practice of this invention comprise one or more primary intermediates together with one or more couplers. The selection of specific intermediates or couplers determines the ultimate color of the treated hair. Such selection is not a critical aspect of the practice of the invention.

A wide variety of primary intermediates can be employed in this invention including, for example:

p-phenylenediamine derivatives such as: benzene-1,4-diamine, 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4,2$-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl )-amino]-ethanol, N-(2-methoxyethyl)-benzene-1,4-diamine, 3-[(4-aminophenyl)amino]propan-1-ol, 3-[(4-aminophenyl)-amino]propane-1, 2-diol, N-{4-[(4-aminophenyl)amino]butyl}benzene-1,4-diamine, and 2-[2-(2-{2-[(2,5-diaminophenyl)oxy]ethoxy}ethoxy)ethoxy]benzene-1,4-diamine;

p-aminophenol derivatives such as: 4-amino-phenol, 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)phenol, and 4-amino-2-fluoro-phenol;

o-aminophenol derivatives such as: 2-amino-phenol, 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, $N^2$, $N^2$-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole-4,5-diamine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}amino)ethanol, 3-(2,4-diaminophenoxy)-propane-1,2-diol, 2-[2-amino-4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2$, $N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine,and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

The primary intermediate(s) and coupler(s) in the aqueous lotion of the invention will normally be employed in equimolar quantities, each at a concentration of about 0.0005% to about 5% by weight, preferably 0.005% to 2.5% by weight.

The selection of the cationic polymer for use in the lotion of this invention is accomplished in relationship to the anionic acrylate/beheneth-25 methacrylate copolymer used in the developer. The test to determine the suitability of the cationic polymer with the anionic copolymer and/or ampho-teric surfactant employed in the lotion is to mix the candi-dates in water at a pH above 7. If an insoluble precipitate forms which does not readily dissolve on the addition of more of the surfactant, then the combination is suitable for use in this invention.

The anionic copolymer for use in the developer will be described in somewhat more detail supra. It is, however, selected on the basis of its insolubility in the developer and the fact that it dissolves to form a gel when the lotion and the developer are mixed.

The presently preferred cationic polymers are quaternary polymers of diallyldialkylammonium salts in which the alkyl groups are the same or different and contain from 1 to 5 carbon atoms such as Merquat 100 (Calgon) or copoly-mers of the above with acrylic acid sold under the names Merquat 280 and Merquat 295, such as those described in U.S. Pat. No. 4,772,462. Surprisingly, it has been observed that the copolymers of diallyldialkylammonium salts with acrylamide, such as that sold under the name Merquat 550, are unsuitable for this purpose.

Other useful polymers include Onamer M (Onyx) a polydimethylbutenyl chloride end-capped with hydroxy-alkyl groups of the formula:

where $R_3$ is a hydroxyalkyl group having 1–5 carbon atoms, preferably 2.

Quaternized polyvinylpyridine where R is alkyl or hydroxyalkyl having 1–5 carbon atoms and X is an anion such as chloride, bromide sulfate or alkylsulfate of the formula:

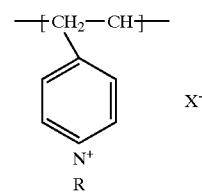

and polymethacrylamidopropyltrimethylammonium chlo-ride

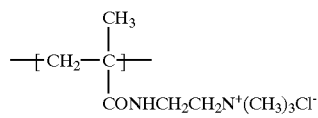

are also useful.

The viscosity of the completely formulated lotion of the invention, when it is ready to mix with the developer, is from about 1 cps to about 5000 cps, preferably 1 cps to 500 cps.

The lotion may contain organic solvents to assist in dissolving the dye precursors. However, it has been observed that in the compositions of this invention, the organic solvent content should be kept at a minimum. More solvent than is necessary to dissolve the precursors may have the effect of retarding diffusion of the precursors into the hair for reaction. Accordingly, the organic solvent con-tent of the lotion may be from 0% by weight to about 5% by weight.

Typically useful solvents include alcohols containing up to three carbon atoms such as ethanol and isopropanol, polyhydroxy alcohols such as propylene or hexylene glycol and lower alkyl ethers thereof such as ethoxy ethers.

Other conventional agents often employed in hair color-ing compositions may be employed in the lotion or in the developer. These include, for example, fragrances, coloring agents and chelating agents. Antioxidants such as sodium sulfite erythorbic acid and ascorbic acid may also be included to inhibit premature oxidation.

The oxidizing composition or developer employed in the invention is an acidic aqueous composition which comprises the selected oxidizing agent together with one or more anionic polymers which are insoluble in water.

The preferred oxidizing agent for use in the developer of the invention is hydrogen peroxide although other peroxides may be employed. These include, for example, urea peroxide, melamine peroxide, perborates and percarbonates such as sodium perborate or percarbonate. The concentra-tion of peroxide in the developer may be from about 0.5% to about 40% by weight, preferably 0.5% to 30% by weight. If the preferred hydrogen peroxide is employed, the con-centration will be from about 0.5% to about 15% by weight, preferably 3% to 13% by weight.

A significant aspect of the practice of this invention is the anionic polymer for use in the developer. It should be stable to the peroxide oxidant, insoluble in the developer and, when the developer is mixed with the lotion, assist in the formation of a gel in which the anionic polymer is soluble. The anionic polymer employed in the developer solution of this invention is an acrylate/beheneth-25 methacrylate copolymer commercially available from Rohm and Haas, Philadelphia, Pa. under the name Aculyn® 28. Although Aculyn® 28 can be employed as the sole anionic copolymer in the developer solution of this invention, other additional anionic polymers, such as for example a copolymer of acrylic or methacrylic acid with their lower alkyl esters (Aculyn® 33) or nonionic thickeners, can also be added to the developer solution as long as their addition does not adversely effect the advantages of the use of Aculyn® 28 polymer's performance.

The concentration of anionic polymer in the developer is from about 0.1% by weight to about 6% by weight, preferably about 0.5% to 4% by weight, most preferably about 1% to 3%, generally about 1.5% by weight. The developer solution will generally contain at least 75% by weight of water, preferably about 75 to 95% or more water.

The structure of Aculyn® 28 copolymer is as follows

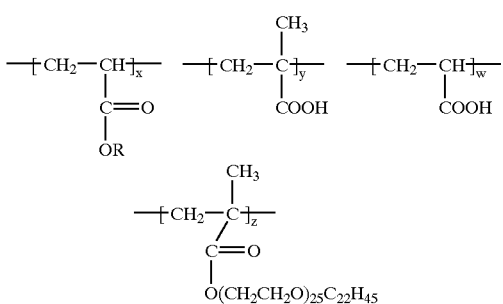

The developer and/or the lotion may also contain from 0 to about 0.2% by weight of a stabilizer such as phenacetin or ethylene diamine tetracetic acid (EDTA); from about 0 to 0.10%, preferably about 0.001% to 0.01 % by weight of an antifoam agent such as simethicone; from about 0 to about 2%, preferably about 0.1% to 0.5% by weight pH buffer, such as for example etidronic acid; and from 0 to about 5%, preferably about 1.5% to 3% of any suitable conditioners, emulsifiers and/or surfactants, particularly conditioners, emulsifiers and surfactants such as PEG-50 tallow amide conditioner, Oleth-2, Oleth-5, Oleth-10 and oleyl alcohol emulsifiers, and $C_{12}$–$C_{15}$ Pareth-3.

The viscosity of the developer as prepared for mixture with the lotion is from about 1 cps to about 5000 cps by weight, preferably 1 cps to 500 cps by weight.

It is desirable but not essential that the viscosities of the lotion and the developer be close to each other. If the difference in viscosities is too great they will be difficult to mix. On shaking the thinner solution will agitate well, but the thicker component will be more difficult to agitate and the rate of blending will be slowed down. One of the significant advantages of the developer solution of this invention is it ability to sheer down (sheer down due to thinning) when the developer solution is dispensed from a squeezable bottle. However, the mixture then recovers its viscosity once applied to provide a non-drip product attribute that is require for a cosmetically acceptable hair dye product.

The pH of the developer is from about 2 to about 6, preferably 2.5 to 4.5, most preferably 2 to 3. Any of a variety of non-toxic acids or buffers may be employed to maintain pH. Etidronic is the most preferred.

The developer solution of this invention can be prepared in the following manner.

Water is heated to about 50° C. to about 60° C. and the buffering agent added. Combine in a premix the anionic polymer conditioner, and all emulsifiers and surfactants, and heat the premix to about 78° C. to about 80° C. Slowly add the heated premix to the heated buffered water solution and mix for approximately 20 minutes until a substantially uniform solution is obtained. Cool the solution with DI water and add the oxidant, e.g. hydrogen peroxide, to the solution at a temperature below about 40° C. Then individually add the thickeners and antifoam agents to the solution and mix the resulting solution until essentially uniform.

The lotion and developer are mixed just before application to the hair. On the hair, they form a stable gel with enough consistency and body to remain on the hair during the complete coloring period without dripping or running. At low levels of active solids of the anionic polymer, e.g. about 1.5%, a hydrogen peroxide solution containing this polymer, when combined with a suitable dye base in the lotion, thickens to an ideal viscosity of about 6,000 to about 30,000 cps. The resulting mixture exhibits the ability to 'sheer down" during mixing to allow the developer/polymer solution to intermingle easily with the dye base components in the lotion, during which time the polymer is neutralized with a portion of the alkali, already present in the lotion composition, and thickening occurs. The primary intermediate and coupler, i.e. the dye precursors diffuse rapidly into the hair together with the oxidizing agent. The dyes form within the hair fiber and, since they are large molecules, remain in the hair so that the color change is permanent. The term "permanent" means that the dye does not readily wash out of the hair with ordinary shampoos. The color achieved with the products of this invention is so stable that it may survive as many as 20 shampoos without noticeable change. Moreover, the use of the acrylate/beheneth-25 methacrylate copolymer in the developer composition of this invention essentially eliminates the drying out effect produced with the prior art anionic polymers. The copolymer of this invention increases significantly the time required for film formation to permit avoidance of the drying out drawback. This had the additional advantage of enabling improved handling and manufacture of peroxide developer solutions. The compositions of this invention produce a hair dye system that has excellent stay-put and application properties, and provide the opportunity to more efficiently deliver conditioning materials resulting in improved product performance.

At the end of the coloring period, the composition is washed from the hair with an ordinary water rinse followed by a shampoo.

The compositions of this invention may be separately provided in a kit or package form ready for mixing by the user, either professional or personal, to initiate the dyeing process. It is preferred to mix them in a mixing vessel for subsequent application to the hair as the gel forms.

The kit provided in accordance with this invention comprises those containers. In the most convenient form, there will be two containers, one containing the lotion, the other the developer. Particularly when a solid oxidant is employed, it may be convenient to package the developer in separate containers one with the oxidizing agent, the other with the anionic polymer in water. With both embodiments of the invention, the ingredients in the aqueous composition of the first container will include the dye precursors, the anionic and/or amphoteric surfactant and the cationic polymer all in the amounts defined above.

The method of the invention comprises applying the mixture to the hair to be colored and allowing it to remain in contact with the hair until the desired hair color has been attained after which the composition is removed from the hair as described above.

The following non-limiting examples are given by way of illustration only.

EXAMPLES 1 TO 4

Dye base lotion formulations were prepared from the following ingredients.

Example 1

| Ingredient | Wt. % |
| --- | --- |
| D. I. water | 57.9151 |
| Propylene glycol | 12.0000 |
| Behentrimonium chloride | 1.0000 |
| Oleth-2 | 2.0000 |
| Oleth-10 | 6.0000 |
| Oleth-5 | 3.5000 |
| Monoethanolamine | 3.5000 |
| Hexylene glycol | 6.0000 |
| Hydroxyethyl cetyldimonium phosphate | 3.0000 |
| Fragrance | 1.0000 |
| Citric acid | 0.5000 |
| Sodium sulfite | 0.2000 |
| EDTA | 0.1000 |
| Erythorbic acid | 0.5000 |
| p-phenylenediamine | 0.4500 |
| p-Aminophenol | 0.7500 |
| 2-Methylresorcinol | 0.4200 |
| Resorcinol | 0.5800 |
| m-Aminophenol | 0.5159 |
| 4-Amino-2-hydroxytoluene | 0.6900 |

Example 2

| Ingredient | Wt. % |
| --- | --- |
| D. I. water | 55.4210 |
| Propylene glycol | 15.0000 |
| Behentrimonium chloride | 1.0000 |
| Oleth-2 | 4.0000 |
| Oleth-10 | 4.0000 |
| Oleth-5 | 3.5000 |
| Monoethanolamine | 3.5000 |
| Hexylene glycol | 6.0000 |
| Hydroxyethyl cetyldimonium phosphate | 3.0000 |
| Fragrance | 1.0000 |
| Citric acid | 0.5000 |
| Sodium sulfite | 0.2000 |
| EDTA | 0.1000 |
| Erythorbic acid | 0.5000 |
| 3-Methyl-p-aminophenol | 0.5000 |
| 2-Methyl naphthol | 0.7000 |
| 1-(2,5-Diaminophenyl)-1,2-ethanediol | 0.6000 |
| 1-(5-Amino-2-hydroxyphenyl0-1,2-diol | 0.4000 |
| p-Phenylenediamine | 0.7000 |
| 4-Amino-2-hydroxytoluene | 0.6900 |

Example 3

| Ingredient | Wt. % |
| --- | --- |
| D. I. water | 54.9151 |
| Propylene glycol | 12.0000 |
| Behentrimonium chloride | 1.0000 |
| Nonoxynol-49 | 2.0000 |
| Oleth-10 | 6.0000 |
| Oleth-5 | 3.5000 |
| Monoethanolamine | 3.5000 |
| Hexylene glycol | 6.0000 |
| Steareth-21 | 3.0000 |
| Fragrance | 1.0000 |
| Citric acid | 0.5000 |
| Sodium sulfite | 0.2000 |
| EDTA | 0.1000 |
| Erythorbic acid | 0.5000 |
| p-phenylenediamine | 0.4500 |
| p-Aminophenol | 0.7500 |
| 2-Methylresorcinol | 0.4200 |
| 2.Methyl-p-aminophenol | 0.5800 |
| m-Aminophenol | 0.5159 |
| 2-Methyl naphthol | 0.6900 |

Example 4

| Ingredient | Wt. % |
| --- | --- |
| D. I. water | 54.9151 |
| Propylene glycol | 12.0000 |
| Behentrimonium chloride | 1.0000 |
| Oleth-2 | 2.0000 |
| Cocoamide propyl betaine | 6.0000 |
| Oleth-5 | 3.5000 |
| Ammonium hydroxide | 3.5000 |
| Hexylene glycol | 6.0000 |
| Hydroxyethyl cetyldimonium phosphate | 3.0000 |
| Fragrance | 1.0000 |
| Citric acid | 0.5000 |
| Sodium sulfite | 0.2000 |
| EDTA | 0.1000 |
| Erythorbic acid | 0.5000 |
| p-phenylenediamine | 0.4500 |
| p-Aminophenol | 0.7500 |
| 2-Methylresorcinol | 0.4200 |
| Resorcinol | 0.5800 |
| m-Aminophenol | 0.5159 |
| 4-Amino-2-hydroxytoluene | 0.6900 |

A developer solution was prepared from the following ingredients.

| Ingredient | Wt % |
| --- | --- |
| D. I. water | 82.9740 |
| Disodium EDTA | 0.0400 |
| Etidronic acid | 0.0800 |
| PEG-50 tallow amine | 1.0000 |
| Oleth-2 | 1.0000 |
| Oleth-5 | 1.0000 |
| Oleyl alcohol | 0.3000 |
| Steareth-21 | 2.0000 |
| Hydrogen peroxide | 5.6000 |
| Aculyn ®-28 | 6.0000 |
| Simethicone | 0.6000 |

Each solution is packaged in a separate container for use as a dyeing kit. Upon discharge of the developer solution from a squeezable container a sheering down is experienced which permits easy mixing with the dye base lotion whereupon desired thickening occurs to provide a non-drip dyeing product.

With the foregoing description of the invention, those skilled in the art will appreciate that modification may be made to the invention without departing from the spirit thereof. Therefore, it is not intended that the scope of the invention be limited to the specific embodiments illustrated and described.

What is claimed is:

1. A high aqueous-content developer formulation for use in a two-part composition for oxidative dyeing of hair, the developer formulation comprising:
   at least about 70% by weight water,
   a peroxide oxidizer, and
   an acrylate/beheneth-25 methacrylate copolymer.

2. A developer formulation of claim 1 wherein the oxidizer is hydrogen peroxide.

3. A developer formulation of claim 2 wherein the hydrogen peroxide is present in an amount of from about 0.5% to about 15% by weight and the acrylate/beheneth-25 methacrylate copolymer is present in an amount of from about 0.5% to about 4% by weight.

4. A two-part aqueous composition for coloring and providing conditioning to human hair and which forms a gel on mixing of the two parts, the two-part aqueous composition comprising:
   (a) an aqueous lotion first part having a pH of from about 7 to about 11 containing from about 0.005% by weight to about 5% by weight of at least one primary intermediate and at least one coupler for the formation of oxidation dyes, from about 0.1% to about 5% by weight of a cationic polymer, from about 0.5% to about 15% by weight of an anionic, nonionic, or amphoteric surfactant or mixture thereof and at least 70% by weight water, wherein the cationic polymer is characterized in that it forms an insoluble precipitate when mixed with said surfactant in water at a pH above 7 and the precipitate does not readily dissolve upon the addition of more of said surfactant; and
   (b) an aqueous developer second part having a pH of from about 2 to about 6 containing from about 0.5% by weight to about 40% by weight of a peroxide oxidizer, at least about 70% by weight water and from about 0.1% by weight to about 6% by weight of an anionic polymer, wherein the anionic polymer is an acrylate/beheneth-25 methacrylate copolymer and is insoluble in the developer but dissolves to form said gel when the lotion and developer are mixed.

5. A composition as in claim 4 wherein:
   a: the pH of the lotion is from 9.0 to 10.5, the primary intermediate and coupler content is from 0.005% to 2.5% by weight, the content of cationic polymer is from 0.5% to 3.0% by weight, the anionic, nonionic, or amphoteric surfactant or mixture thereof content is from 2% to 8% by weight; and
   b: the pH of the aqueous developer is from 2.5 to 4.5, the peroxide oxidizer content is from 0.5% to 30% by weight hydrogen peroxide, the anionic polymer content is 0.5% to 4% by weight, and the water content is from about 70% to about 95% by weight.

6. A composition as in claim 4 wherein the developer contains from about 0.5% to about 15% by weight of hydrogen peroxide and the anionic copolymer is present in the developer formulation in an amount of from about 1% to 3% by weight.

7. A composition as in claim 5 wherein the developer contains from about 3% to about 13% by weight of hydrogen peroxide and about 1.5% by weight of the anionic copolymer.

8. A composition as in claim 5 wherein:
   the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, and cocoamphopropylsulfonate; and the primary intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one,and 1H-indol-6-ol, and 2-aminopyridin-3-ol.

9. A kit containing a two-part aqueous composition which forms a gel on mixing of the two parts for coloring human hair comprising separate first and second containers:
   (a) the first container containing an aqueous lotion first part having a pH of from about 7 to about 11 containing from about 0.005% to about 5% by weight of at least one primary intermediate and at least one coupler for the formation of oxidation dyes, from about 0.1% to about 5% by weight of a cationic polymer, from about 0.5% to about 15% by weight of an anionic, nonionic, or amphoteric surfactant or mixture thereof and at least 70% by weight water, wherein the cationic polymer is characterized in that it forms an insoluble precipitate when mixed with said surfactant in water at a pH above 7 and said precipitate does not readily dissolve upon the addition of more of said surfactant; and
   (b) the second container containing an aqueous developer second part having a pH of from about 2 to about 6 containing from about 0.5% to about 40% by weight of a peroxide oxidizer and from about 0.1% to about 6% by weight of an acrylate/beheneth-25 methacrylate copolymer and is insoluble in the developer but dissolves to form said gel when the lotion and developer are mixed.

10. A kit as in claim 9 wherein:
   a: the pH of the lotion is from 9.0 to 10.5, the primary intermediate and coupler content is from 0.005% to 2.5% by weight, the content of cationic polymer is from 0.5% to 2.0% by weight, the anionic, nonionic or amphoteric surfactant or mixture thereof content is from 2% to 8% by weight; and
   b: the pH of the aqueous developer is from 2.5 to 4.5, the peroxide oxidizer content is from 0.5% to 30% by weight,hydrogen peroxide, the anionic copolymer content is about 0.5% to about 4% by weight, and the water content is about 70% to about 95% by weight.

11. A kit as in claim 9 wherein the developer contains from about 0.5% to about 15% by weight of hydrogen peroxide and the anionic copolymer is present in an amount of from about 1% to 3% by weight.

12. A kit as in claim 10 wherein the developer contains from about 3% to about 13% by weight of hydrogen peroxide and the anionic copolymer is present in an amount of about 1.5% by weight.

13. A kit as in claim 10 wherein:

the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropylsulfonate, stearyl betaine, cocamidopropyl dimethylarnine propionate, cocoamphoglycinate, cocoamphocarboxypropionate, cocoaphocarboxyglycinate, cocobetaine, cocoamphopropionate, and cocoamphopropylsulfonate; and the primary intermediate is selected from the group consisting of the primary intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one,and 1H-indol-6-ol, and 2-aminopyridin-3-ol.

14. A method of coloring human hair which comprises contacting the hair with a mixture of a two-part aqueous composition which forms a gel on mixing of the two parts comprising:

(a) an aqueous lotion first, part having a pH of from about 7 to about 11 containing from about 0.005% to about 5% by weight of at least one primary intermediate and at least one coupler for the formation of oxidation dyes, from about 0.1% to about 5% by weight of a cationic polymer, from about 0.5% to about 15% by weight of an anionic, nonionic or amphoteric surfactant or mixture thereof and at least 70% by weight water, wherein the cationic polymer is mixed with the surfactant in water at a pH above 7 to form an insoluble precipitate which does not readily dissolve upon the addition of more of the surfactant; and (b) an aqueous developer second part having a pH of from about 2 to about 6 containing from about 0.5% to about 40% by weight of a peroxide oxidizer, at least about 70% by weight water and from 0.1% to about 6% by weight of a water insoluble anionic polymer; wherein the anionic polymer is an acrylate/beheneth-25 methacrylate copolymer and is insoluble in the developer but dissolves to form said gel when the lotion and developer are mixed, and maintaining such contact until the hair is permanently colored.

15. A method as in claim 14 wherein:

a: the pH of the lotion is from 9.0 to 10.5, the primary intermediate and coupler content is from 0.005% to 2.5% by weight, the content of cationic polymer is from 0.5% to 3.0% by weight, the anionic, nonionic or amphoteric surfactant content is from 2% to 8% by weight; and b: the pH of the aqueous developer is from 2.5 to 4.5, the peroxide oxidizer content is from 0.5% to 30% by weight, the anionic polymer content is 0.5% to 4% by weight, and the water content is about 70% to about 95% by weight.

16. A method as in claim 14 wherein the developer contains from about 0.5% to about 15% by weight of hydrogen peroxide and the anionic copolymer is present in an amount of from about 1% to about 3% by weight.

17. A method as in claim 15 wherein the developer contains from about 3% to about 13% by weight of hydrogen peroxide and the anionic copolymer is present in an amount of about 1.5% by weight.

18. A method as in claim 15 wherein:

the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoaphocarboxyglycinate, cocobetaine, cocoamphopropionate, and cocoamphopropylsulfonate; and the primary intermediate is selected from the group consisting of the primary intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one,and 1H-indol-6-ol, and 2-aminopyridin-3-ol.

19. In a method for oxidative coloring of hair with a two-part dyeing composition comprising a first dye base lotion part and a second developer formulation the improvement comprising using as the developer formulation a formulation comprising:

at least about 70% by weight water, a peroxide oxidizer, and a substantially water insoluble anionic acrylate/beheneth-25 methacrylate copolymer.

20. The method of claim 19 wherein the oxidizer is hydrogen peroxide and the anionic copolymer is present in the developer formulation in an amount of from about 1% to 3% by weight.

21. A two part aqueous composition for coloring and providing conditioning to human hair and which forms a gel on mixing of the two parts, the two-part aqueous composition comprising:

(a) an aqueous lotion first part having a pH of from about 7 to about 11 containing from about 0.005% by weight to about 5% by weight of at least one primary intermediate and at least one coupler for the formation of oxidation dyes, from about 0.5% to about 15% by weight of an anionic, nonionic, or amphoteric surfactant or mixture thereof, and water, and (b) an aqueous developer second part having a pH of from about 2 to about 6 containing from about 0.5% by weight to about 40% by weight of a peroxide oxidizer, at least about 70% by weight water, and from about 0.1% by weight to about 6% by weight of an acrylate/beheneth-25 methacrylate copolymer that is insoluble in the developer, said copolymer dissolving to form said gel when the lotion and developer are mixed.

22. A composition as in claim 21 wherein:

a: the pH of the lotion is from 9.0 to 10.5, the primary intermediate and coupler content is from 0.005% to 2.5% by weight, the anionic, nonionic, or amphoteric surfactant or mixture thereof content is from 2% to 8% by weight; and b: the pH of the aqueous developer is from 2.5 to 4.5, the peroxide oxidizer content is from 0.5% to 30% by weight hydrogen peroxide, the acrylate/beheneth-25 methacrylate copolymer content is 0.5% to 4% by weight, and the water content is from about 70% to about 95% by weight.

23. A composition as in claim 21 wherein the lotion contains above about 54.9151% water by weight.

24. A composition as in claim 21 further comprising from about 0.1% to about 5% by weight of a cationic polymer, wherein the cationic polymer is mixed with the surfactant in water at a pH above 7 to form an insoluble precipitate which does not readily dissolve upon the addition of more of the surfactant.

\* \* \* \* \*